United States Patent
Yoshida et al.

(10) Patent No.: US 8,899,831 B2
(45) Date of Patent: Dec. 2, 2014

(54) RADIOGRAPHIC APPARATUS

(75) Inventors: Yutaka Yoshida, Kanagawa (JP);
Yusuke Kitagawa, Kanagawa (JP);
Katsumi Shimada, Kanagawa (JP);
Noriaki Ida, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 528 days.

(21) Appl. No.: 13/407,192

(22) Filed: Feb. 28, 2012

(65) Prior Publication Data

US 2012/0250825 A1 Oct. 4, 2012

(30) Foreign Application Priority Data

Mar. 31, 2011 (JP) ................................ 2011-079262

(51) Int. Cl.
*H01L 27/146* (2006.01)
*H01L 31/115* (2006.01)
*H05G 1/08* (2006.01)
*A61B 6/00* (2006.01)
*G03B 42/04* (2006.01)

(52) U.S. Cl.
CPC ............. *A61B 6/4233* (2013.01); *A61B 6/4283* (2013.01); *A61B 6/56* (2013.01); *A61B 6/4021* (2013.01); *G03B 42/047* (2013.01); *G03B 2206/008* (2013.01)
USPC ............. 378/169; 378/87; 378/162; 378/172; 378/210; 250/370.09; 250/370.08; 250/559.46

(58) Field of Classification Search
USPC ............. 378/29, 87, 162, 169, 172, 189, 210, 378/928; 250/370.08, 370.09, 559.07, 250/557.08, 559.46
See application file for complete search history.

(56) References Cited

U.S. PATENT DOCUMENTS

| | | | | |
|---|---|---|---|---|
| 7,015,478 | B2* | 3/2006 | Yamamoto | 250/370.09 |
| 7,813,942 | B2* | 10/2010 | Rose | 705/3 |
| 8,155,406 | B2* | 4/2012 | Mattiuzzi | 382/128 |
| 8,471,213 | B2* | 6/2013 | Yagi et al. | 250/370.09 |
| 8,558,186 | B2* | 10/2013 | Kondou | 250/370.09 |
| 2004/0114725 | A1* | 6/2004 | Yamamoto | 378/189 |
| 2010/0155614 | A1* | 6/2010 | Yagi et al. | 250/370.09 |
| 2011/0108732 | A1* | 5/2011 | Watanabe | 250/370.08 |
| 2012/0199750 | A1* | 8/2012 | Kondou | 250/370.09 |

FOREIGN PATENT DOCUMENTS

| | | |
|---|---|---|
| JP | 2001-340326 A | 12/2001 |
| JP | 2002-336225 A | 11/2002 |
| JP | 2003-199736 A | 7/2003 |
| JP | 2004-173907 | 6/2004 |
| JP | 2008-142094 A | 6/2008 |
| JP | 2009-297187 A | 12/2009 |
| JP | 2010-115390 | 5/2010 |

* cited by examiner

*Primary Examiner* — Bernard E Souw
(74) *Attorney, Agent, or Firm* — Jean C. Edwards, Esq.; Edwards Neils PLLC

(57) ABSTRACT

A radiographic apparatus includes an image acquisition controller for controlling operation of more than one electronic cassette. For signal communication between the image acquisition controller and the electronic cassettes, each electronic cassette may be connected to a communication cable. These communication cables are connected to a switching hub that intermediates communication between the electronic cassettes and the image acquisition controller. The radiographic apparatus includes multiple power supplies corresponding in number to the electronic cassettes. Each electronic cassette may be connected to one power supply through a power cable separately from the communication cable.

14 Claims, 10 Drawing Sheets

RADIOGRAPHIC APPARATUS

CROSS-REFERENCE TO RELATED APPLICATIONS

The present application claims priority from Japanese Patent Application No. 2011-079262, filed Mar. 31, 2011, the contents of which are herein incorporated by reference in their entirety.

BACKGROUND OF THE INVENTION

1. Field of the Invention

The present invention relates to a radiographic apparatus that acquires radiographic images when exposed to radioactive rays.

2. Description of the Related Art

An x-ray radiography system, an example of radiography systems, includes an x-ray projector for projecting x-rays toward a subject and a radiographic apparatus for acquiring x-ray images of the subject from the x-rays having been projected from the x-ray projector and penetrating through the subject. The x-ray projector includes an x-ray source, a radiation source controller, and an activation switch for inputting an x-ray radiation start signal. The radiographic apparatus includes an x-ray image detector for detecting a radiographic image or x-ray image from the x-rays having been penetrating through the subject, and an imaging controller for controlling operation of the x-ray image detector.

An x-ray image detector using a flat panel detector (FPD) in place of conventional x-ray film or imaging plates (IP) has recently been widely spread. The FPD has a large number of pixels arranged in a matrix, to accumulate signal charges corresponding to incident amounts of x-rays on the respective pixels. The FPD converts the signal charges accumulated in the respective pixels to a voltage signal through a signal processing circuit, to detect an x-ray image representative of graphic information on the subject, and output the detected x-ray image as digital image data.

Portable x-ray image detectors, called electronic cassettes, have also been used in practice, which contains a flat panel detector in a rectangular box-shaped body. The plane size of the electronic cassette 21 is about the same as those of radiographic film cassettes and IP cassettes. The electronic cassette can be mounted in a conventional radiographic stand or table which is adapted to the film cassette or IP cassette. In addition, the electronic cassette can be used independently. For example, in order to image such a site of a test subject that is hard to image using the electronic cassette as mounted in the stationary radiographic stand or table, the electronic cassette may be put on a bed with the test subject or may be held directly by the test subject. Moreover, the electronic cassette may be carried around for use in home medical care or emergency medical care at accident sites or disaster sites.

The electronic cassettes include wired types and wireless types. The wired type electronic cassette is connected to a cable for signal transmission from and to the imaging controller or for power-supply from a power source, as disclosed for example in U.S. Patent Application Publication No. 2004/0114725 corresponding to (JPA 2004-173907) and JPA 2010-115390. In U.S. Patent Application Publication No. 2004/0114725, an imaging controller (system control section) and a power supply are integrated into a unit, and a composite cable connected to the electronic cassette is connected through a connector to another composite cable that is connected to the imaging controller and the power supply. The first prior art also discloses an embodiment, in which a battery for power-supply is built in the cassette, and a wireless module for wireless communication is attached to a composite cable that is connected to the cassette.

The second prior art discloses a radiographic cassette holding device, a radiographic stand or table, for mounting the electronic cassette during the radiography. The radiographic cassette holding device is provided with a connector that may be connected to a socket or connector of the electronic cassette through a direct contact or the like, to supply the electronic cassette with power from an external commercial power source. Through this connector, the electronic cassette may also exchange data with the imaging controller.

In a hospital having multiple radiography studios, each studio is usually installed with complete system components so that imaging with the electronic cassette may be executed in parallel in any studio. In that case, the electronic cassette may be moved from one studio to another. If the cable to be connected to the electronic cassette should also be moved across the studios along with the cassette, the cable could tangle in other medical equipment. To avoid such inconvenience, at least one cable is fixedly installed in each studio in the practice, so that it is only necessary to carry about the electronic cassette and connect it to the stationary cable to use it in each studio.

As described in the first prior art, the composite cable for the electronic cassette consists of a couple of cables which are respectively connected to the imaging controller and the power supply. In one conventional example, these cables are bundled together into a composite cable at an output point proximate to the imaging controller and the power supply. Alternatively, where the imaging controller and the power supply are built in a unit, cables from the imaging controller and the power supply are bundled into a composite cable inside the unit housing, and the composite cable is extended from the housing.

The imaging controller and the power supply are conventionally installed in every radiographic studio. This is because at least a power supply unit is necessary in each studio to carry out the imaging with the electronic cassette in parallel or simultaneously in the multiple radiography studios. Since the imaging controller is conventionally coupled to the power supply unit through the bundling of their cables into one composite cable, the imaging controller has also been installed in every radiographic studio. It may be possible to branch the composite cable into two cables at a point proximate to the power supply unit and elongate the cable to the imaging controller so as to share one imaging controller with multiple studios while installing the power supply unit in each radiographic studio.

However, the elongated cables from the respective studios to the shared imaging controller would complicate the wiring across the studios or could hinder the radiographic operation, for example, by getting tangled with the leg of the radiologist or the patient. The same problem could occur in the above mentioned prior art systems. Installing multiple imaging controllers aside from multiple power supply units, however, requires greater space and higher cost.

SUMMARY OF THE INVENTION

In view of the foregoing, an object of the present invention is to provide a space-saving low-cost radiography system.

According to the present invention, a radiographic apparatus comprises a power cable connectable to an electronic cassette; a power supply for supplying power to the electronic cassette, the power supply being connected directly with the power cable; a communication cable provided separately from the power cable; and an image acquisition controller being communicable with the electronic cassette through the communication cable, to control operation of the electronic cassette.

The radiographic apparatus preferably includes multiple power supplies, the same number of power cables and the same number of communication cables as the power supplies, and only one image acquisition controller.

In one embodiment, the radiographic apparatus may include a line concentrator for intermediating communication between the image acquisition controller and multiple electronic cassettes through the communication cables.

Preferably, communication cables connectable to the electronic cassettes and a communication cable directly connected with the image acquisition controller are connected to each other at the line concentrator.

In a case where a composite cable bundling a communication cable and a power cable into a string is connectable to an electronic cassette, the radiographic apparatus may preferably include a first transporter that connects with the composite cable to separate the composite cable into the communication cable and the power cable.

In one embodiment, the communication cable from the transporter and a communication cable directly connecting with the image acquisition controller are connected to each other at the line concentrator.

In another embodiment, the communication cable from the transporter may directly be connected with the image acquisition controller, and the power cable from the transporter may directly be connected with the power supply.

In alternative embodiments, the radiographic apparatus may include a second transporter having a wireless communication device and a wireless LAN for communication with the wireless communication device of the second transporter. An access point of the wireless LAN and a communication cable directly connecting with the image acquisition controller may be connected to each other at the line concentrator.

The first or the second transporter may be mounted on or in a radiographic cassette holding device, to which the electronic cassette is detachably attachable. Preferably, the first or the second transporter is detachably attachable to the radiographic cassette holding device.

In one embodiment, a radiographic cassette holding device for detachably attaching an electronic cassette may be provided with a connector, which is connected with a socket of the electronic cassette to connect the electronic cassette to the communication cable and the power cable when the electronic cassette is attached to the radiographic cassette holding device. The communication cable extending from the connector and a communication cable directly connecting with the image acquisition controller may be connected to each other at the line concentrator. Alternatively, the communication cable and the power cable extending from the connector may be respectively connected directly with the image acquisition controller and the power supply.

Preferably, the image acquisition controller and the line concentrator are connected to each other through a LAN that is developed within a hospital.

According to the present invention, the power cable and the communication cable are provided separately from each other. Therefore, multiple electronic cassettes may be individually supplied from the power supplies through the power cables, while only one image acquisition controller may communicate with the multiple electronic cassettes through the communication cables. Thus, the present invention will provide higher flexibility in installing the power supply and the image acquisition controller, providing a space-saving and low-cost radiographic apparatus.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
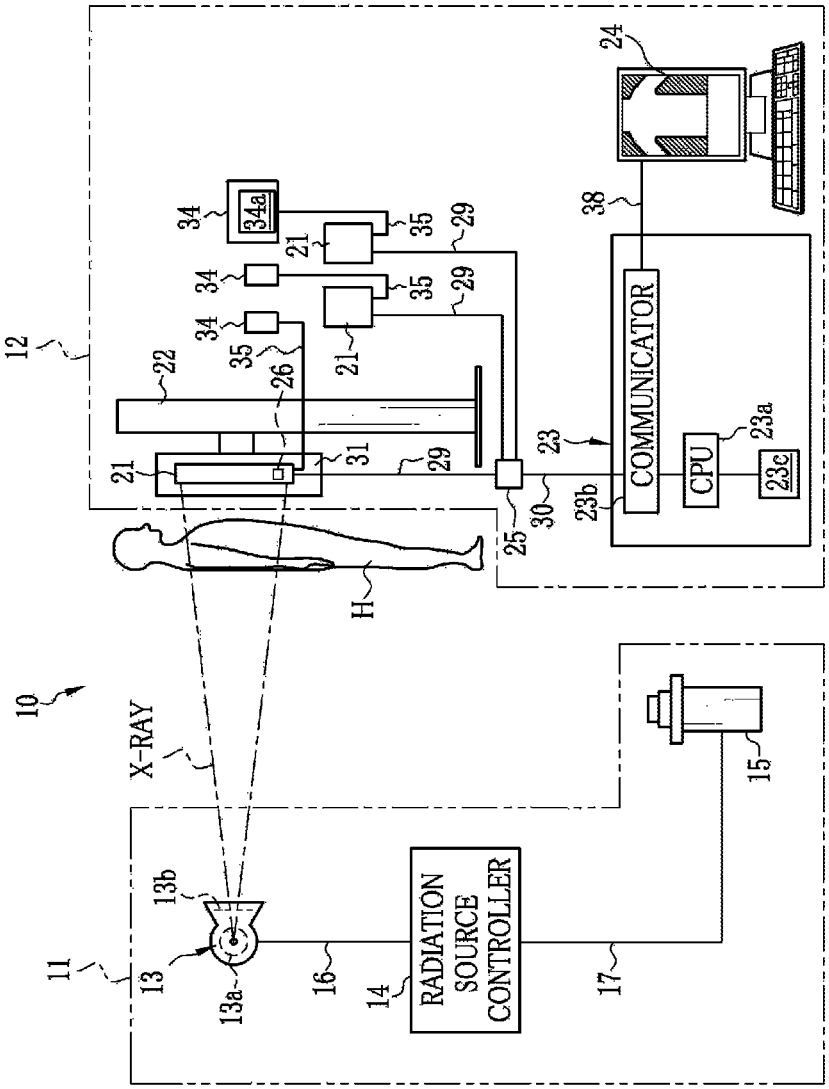
FIG. 1 is a diagram schematically illustrating an x-ray radiography system.

In FIG. 1, an x-ray radiography system 10 consists of an x-ray projector 11 and radiographic equipment 12. The x-ray projector 11 consists of an x-ray source 13, a radiation source controller 14 for controlling the x-ray source 13, and an activator switch 15. The x-ray source 13 has an x-ray tube 13a for radiating x-rays and a collimator 13b for limiting the radiation field of x-rays from the x-ray tube 13a.

The x-ray tube 13a has a cathode which includes a filament for emitting thermions and an anode or target against which the thermions strike to radiate x-rays. The target is a rotary anode shaped into a round disc, which is rotatable to move its focus on a circular orbit, thereby to diffuse thermal energies radiated from the focus when the thermions strike against the focus. The collimator 13b is made of lead plates that block x-rays. The lead plates are put together in a double-cross formation to form a center aperture for letting x-rays pass through it. The lead plates are movable to change the size of the center aperture so as to limit the radiation field to a suitable range.

The radiation source controller 14 includes a high voltage generator for supplying a high voltage to the x-ray source 13, and a controller for controlling tube voltage, tube current and x-ray radiation time, wherein the tube voltage determines energy spectra of x-rays from the x-ray source 13, and the tube current determines the amount of radiation per unit time. The high voltage generator generates the high tube voltage by boosting an input voltage through a transducer, and supplies the tube voltage as the driving power to the x-ray source 13 through a high voltage cable 16. In the present embodiment, the x-ray projector 11 is not capable of communicating with the radiographic equipment 12. Imaging conditions or acquisition settings, including the tube voltage, the tube current and the x-ray radiation time, may be manually set by a radiologist or operator using an operation panel of the radiation source controller 14.

The activator switch 15 is operated by the radiologist, and is connected to the radiation source controller 14 through a signal cable. The activator switch 15 may be a two-step push button switch that outputs a warm-up start signal for staring warming up the x-ray source 13 upon being pushed to the first step. Thereafter, upon being pushed further to the second step, the activator switch 15 outputs a radiation start signal for letting the x-ray source 13 start radiations. These signals are fed through the signal cable 17 to the radiation source controller 14.

The radiation source controller 14 controls the operation of the x-ray source 13 according to the control signals from the activator switch 15. Upon receipt of the warm-up start signal, the radiation source controller 14 actuates a heater to pre-heat the filament and causes the target to start rotating. The warm-up operation is to heat the filament up to a predetermined temperature and set the rotation of the target at a predetermined velocity. It takes about 200 msec. to 1500 msec. for the warm-up operation. The radiologist should input the radiation start signal in the time necessary for completing the warm-up operation after inputting the warm-up start signal.

Upon receipt of the radiation start signal, the radiation source controller 14 starts supplying the power to the x-ray source 13 and also activates a timer to start measuring the duration of the x-ray radiation. When a given radiation time is over, the radiation source controller 14 stops radiation from the x-ray source 13. The x-ray radiation time varies depending upon other exposure conditions, but the maximum x-ray radiation time for acquisition of a still image is mostly set in the range of about 500 msec. to about 2 sec. Therefore, the radiation time is limited up to the maximum radiation time.

In the illustrated example, the radiographic equipment 12 consists of three electronic cassettes 21, a radiographic stand 22, an image acquisition controller 23, a console 24, and a switching hub 25. Only one of the three cassettes 21 is selectively mounted in the radiographic stand 22. These electronic cassettes 21 may serve for different applications, e.g. for imaging in different postures, or may be different in size, or may be the same type.

The electronic cassette 21 includes a radiation sensor 26 in addition to a flat panel detector (FPD) 27 (see FIG. 3) and a portable housing 28 containing the FPD 27. The electronic cassette 21 is to detect an x-ray image or radiograph of a test subject or patient H when it receives x-rays that have been projected from the x-ray source 13 and penetrate through the test subject H. The electronic cassette 21 has a flat planer body having substantially rectangular top and bottom surfaces. The plane size of the electronic cassette 21 is about the same as those of radiographic film cassettes and IP cassettes.

The radiation sensor 26 is placed adjacent to an imaging area of the FPD 27. The radiation sensor 26 outputs a radiation detecting signal corresponding to an incident amount of x-rays when it receives the x-rays. The radiation detecting signal is fed through a communication cable 29, the switching hub 25 and a communication cable 30 to the imaging controller 23. The imaging controller 23 monitors the signal level of the radiation detecting signal to detect that the x-ray source 13 starts x-ray radiation.

Figure 2:
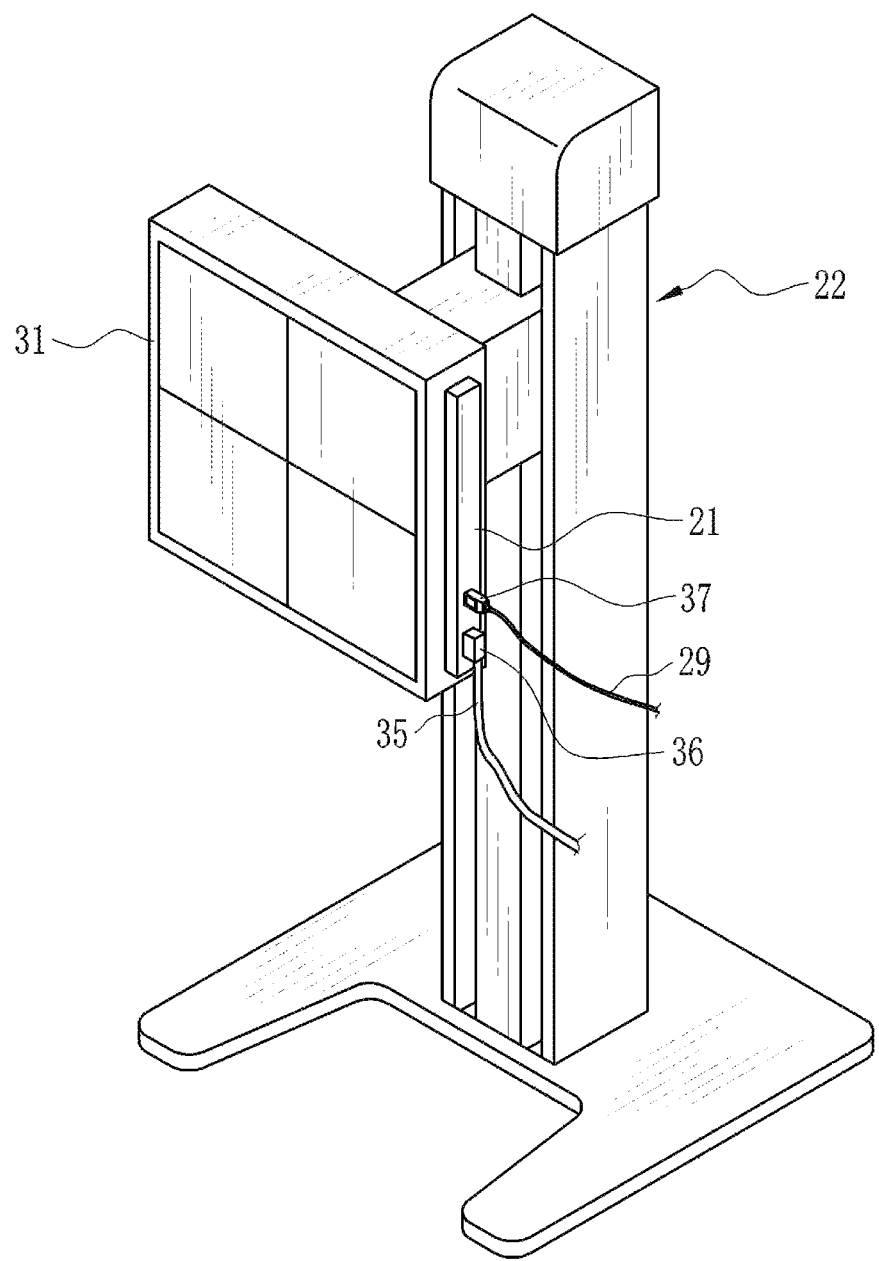
FIG. 2 is a perspective view of a radiographic stand having an electronic cassette mounted in a holder.

As shown in detail in FIG. 2, the radiographic stand 22 has a holder 31 for removably mounting and holding the electronic cassette 21 therein in a position where an x-ray sensitive surface of the cassette 21 is opposed to the x-ray source 13. Having approximately the same size housing 28 as the film cassettes and IP cassettes, the electronic cassette 21 can be mounted to conventional radiographic stands or tables for the film cassettes or IP cassettes. It is to be noted that the radiographic stand 22 for imaging the test subject H in the upright position may be replaced with a radiographic table for imaging the test subject H in the recumbent position. The electronic cassette 21 may also be placed on a bed for the test subject H or held by the test subject H for the radiography.

Figure 3:
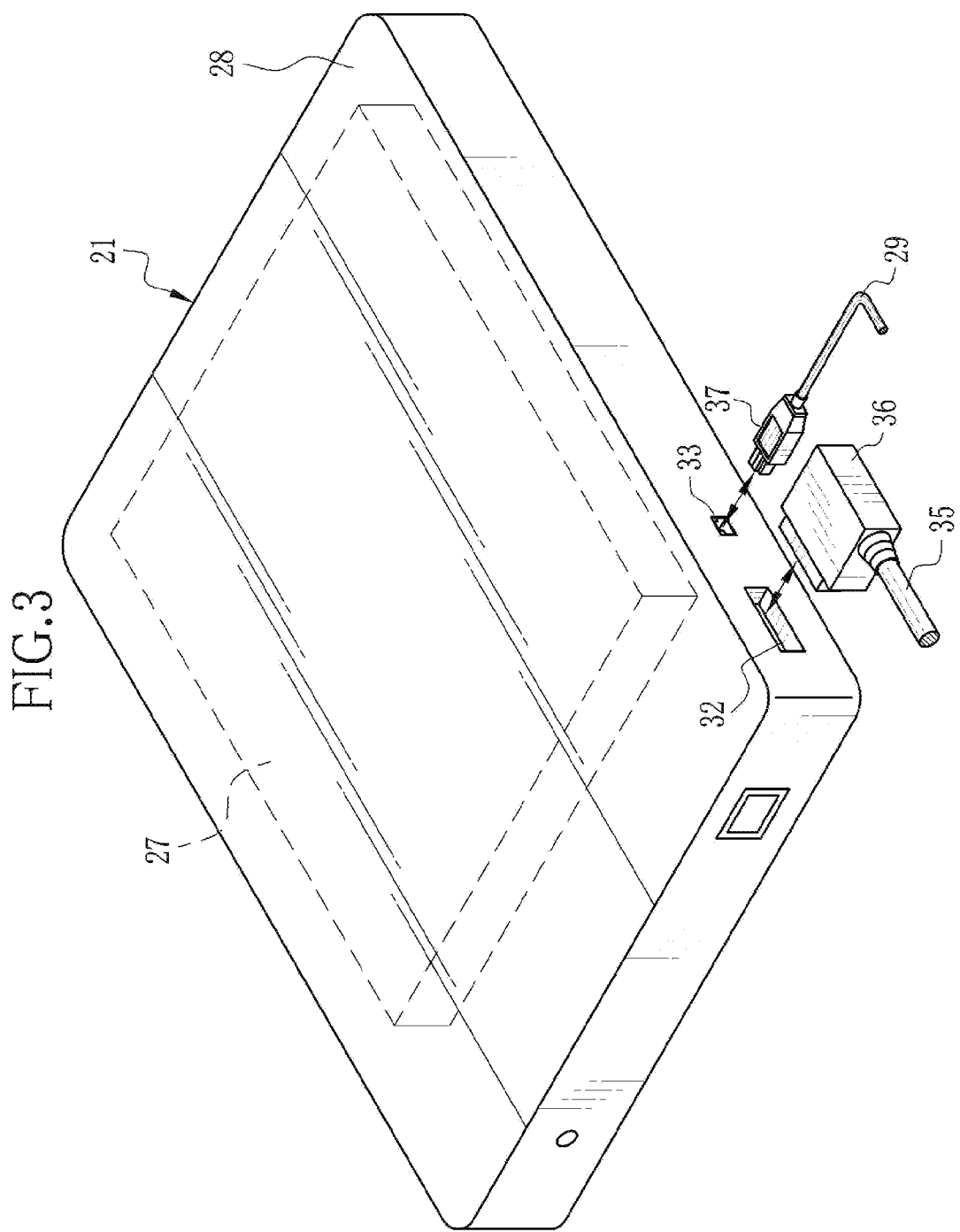
FIG. 3 is a perspective view of the electronic cassette.

Referring to FIG. 3, the FPD 27 contained in the electronic cassette 21 may be of an indirect conversion type that has thin film transistors (TFTs), a matrix substrate having pixels arranged in a matrix, each pixel being an x-ray detection element, and a scintillator (a phosphor) for converting x-rays to visible rays. The visible rays are converted to electric charges through the pixels of the matrix substrate. The scintillator is positioned to face to the whole imaging area in which the pixels are arranged. Note that the FPD 27 may be of a direct conversion type using a conversion layer that converts x-rays directly to electric charges; the conversion layer may be made of amorphous selenium.

The FPD 27 accumulates electric charges in the x-ray detection elements (pixels) while the TFTs are off. The accumulated electronic charges correspond to the incident amounts of x-rays on the respective pixels. By turning the TFTs off, the accumulated charges are read out from the x-ray detection elements. Then the charges are converted to an analog voltage signal through integrating amplifiers, and the voltage signal is converted to digital image data through an analog-to-digital converter.

As well known in the art, dark charges corresponding to dark currents are accumulated in the pixels. Because the dark charges are noises for the image data, the FPD 27 repeats a resetting operation to sweep off the dark charges until the radiation sensor 26 detects the start of x-ray radiation. Upon the start of x-ray radiation being detected by the radiation sensor 26, the FPD 27 proceeds from the resetting operation to an accumulating operation. In a predetermined time after the start of accumulating operation, the FPD 27 proceeds from the accumulating operation to a reading operation for reading out the accumulated charges as the voltage signal.

Sockets 32 and 33 are provided on one side of the electronic cassette 21. The socket 32 is for connecting the electronic cassette 21 to a power supply 34 (see FIG. 1) through a power cable 35, and the socket 33 is for connecting the electronic cassette to the image acquisition controller 23 through the communication cable 29. A connecter 36 of the power cable 35 is plugged in the socket 32, whereas a connecter 37 of the communication cable 29 is plugged in the socket 33.

Figure 4:
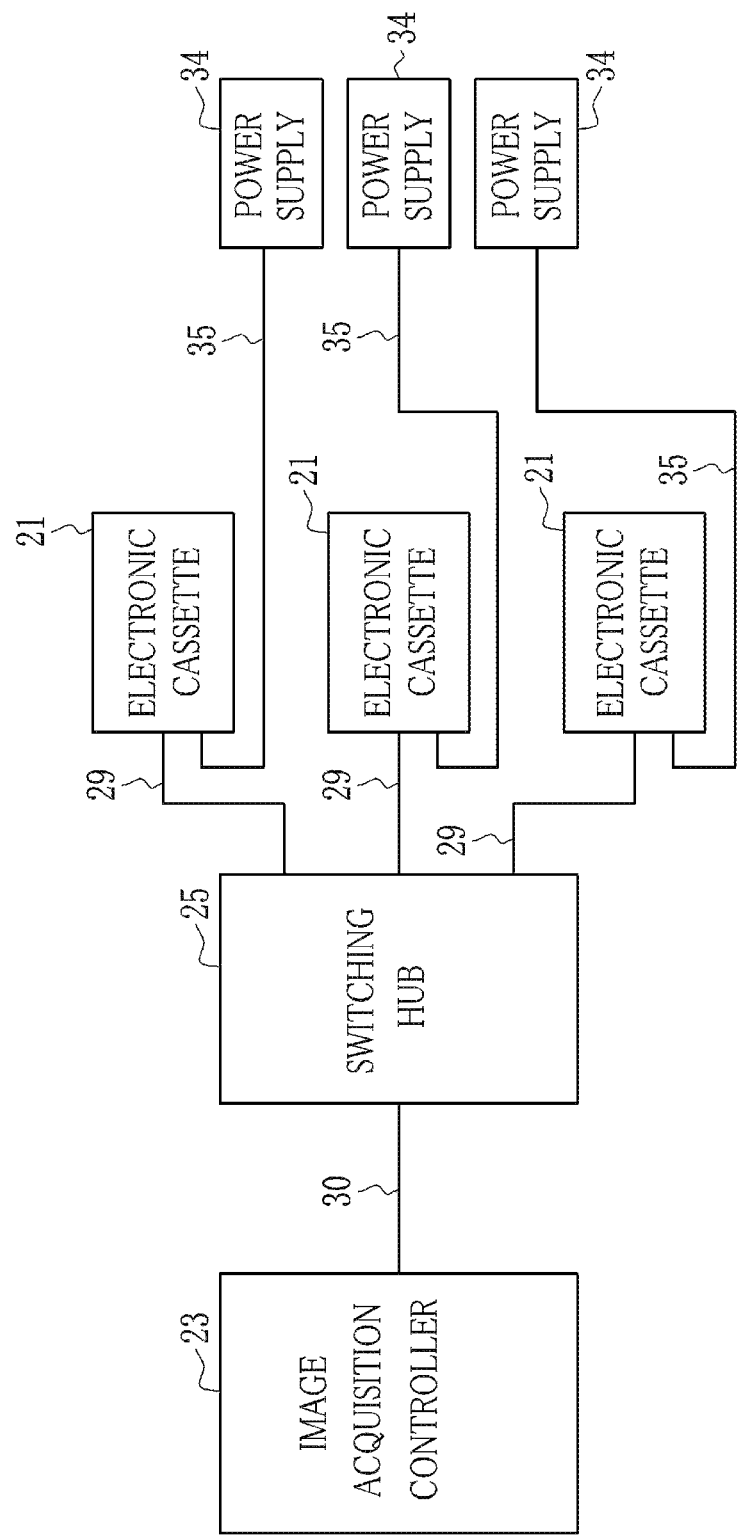
FIG. 4 is a block diagram illustrating the circuitry of a radiographic apparatus in accordance with a first embodiment of the invention.

As shown in FIGS. 1 and 4, three power cables 35 connected to the three electronic cassettes 21 are respectively coupled to three power supplies 34. On the other hand, three communication cables 29 are coupled to one switching hub 25. The switching hub 25 and the image acquisition controller 23 are interconnected through the communication cable 30. The communication cables 29 and 30 may be commercially available LAN cables.

The power supplies 34 individually include an AC/DC converter 34a for converting AC voltage from an external commercial power source to DC voltage for the electronic cassette 21.

The switching hub 25 serves as a line concentrator and also intermediates the signal exchange between the image acquisition controller 23 and the individual electronic cassettes 21. The switching hub 25 may be a commercially available signal transit device that determines the destination of the transmitted signal based on a MAC address or IP address that is included in the signal to designate the image acquisition controller 23 or any of the electronic cassettes 21, to send the signal to the determined destination.

The image acquisition controller 23 is communicably connected to the electronic cassettes 21 through the respective communication cables 29 and the communication cable 30. The image acquisition controller 23 consolidates the operation of the electronic cassettes 21. Specifically, the image acquisition controller 23 sends acquisition setting data to the electronic cassette 21 to set up conditions for signal processing in the FPD 27, such as amplification rate for the voltage signal read out from the pixels, and indirectly controls the resetting, accumulating and reading operations of the FPD 27. The image acquisition controller 23 also receives image data output from the electronic cassette 21.

Referring back to FIG. 1, the image acquisition controller 23 includes a CPU 23a for comprehensive control of the controller 23, a communicator 23b for communication with the electronic cassettes 21 through the communication cables 29 and 30 and communication with the console 24 through a communication cable 38, and a memory 23c. The communicator 23b and the memory 23c are connected to the CPU 23a. The memory 23c stores control programs to be executed by the CPU 23a.

The console 24 transmits the acquisition setting data to the image acquisition controller 23 and receives data of acquired x-ray images from the image acquisition controller 23. The console 24 renders the image data with various processes, such as offset correction and gain correction. Based on the processed image data, x-ray images are displayed on a screen of the console 24. The processed image data is also stored in a data storage device, such as a hard disc or a memory within the console 24 or an image database server that is communicably connected to the console 24 through a network.

The console 24 may receive examination orders, each including information on the sex and age of the patient, the target site of imaging, the purpose of imaging, etc., and display the received examination orders. The examination orders may be issued by external systems, such as a hospital information system (HIS) and a radiological information system (RIS), which manage information on patients and information on x-ray examinations. The examination orders may also be manually input by the operator or radiologist. Before executing the imaging, the radiologist inputs acquisition settings through an operation screen on the console 24 while checking the contents of the designated examination order, which are displayed on the screen. Alternatively, the image acquisition controller 23 may be provided with the function of the console 24. In that case, there is no need for providing a console separately from the image acquisition controller 23.

Now the operation of the x-ray radiography system 10 will be described with respect to the above-described embodiment.

To radiograph in the x-ray radiography system 10, one of the electronic cassettes 21 is mounted in the radiographic stand 22, and the height of the cassette 21 is adjusted to the position of the target site of the test subject H. Next, the height and radiation field of the x-ray source 13 are adjusted to the height of the electronic cassette 21 and the size of the target site. Thereafter, the electronic cassette 21 is powered on. Then, the acquisition settings are entered through the console 24 and applied through the image acquisition controller 23 to the electronic cassette 21. The acquisition settings are also applied to the radiation source controller 14.

When the system 10 thus gets ready for an exposure, the radiologist pushes the activator switch 15 to the first step, upon which the activator switch 15 sends out the warm-up start signal to the radiation source controller 14, starting warming up the x-ray source 13. When the predetermined time has elapsed thereafter, the activator switch 15 is pushed to the second step to send out the radiation start signal to the radiation source controller 14, upon which the x-ray source 13 starts x-ray radiation.

Meanwhile, the FPD 27 continually detects whether the x-ray source 13 starts x-ray radiation or not while repeating the resetting operation for resetting the dark charges. When the start of x-ray radiation is detected, all of the TFTs of the FPD 27 are turned off to start the accumulating operation in the electronic cassette 21. When a radiation time given as one exposure condition by the acquisition settings has elapsed from the start of x-ray radiation, the radiation source controller 14 stops the x-ray radiation. Also the FPD 27 terminates the accumulating operation in a predetermined time corresponding to the radiation time, and then starts the reading operation. In the reading operation, signal charges accumulated in the pixels are readout sequentially from the first line of the pixel matrix. The signal charges read out from the pixel matrix are converted to a frame of x-ray image data and transmitted through the communication cable 29, the switching hub 25 and the communication cable 30 to the image acquisition controller 23. After the reading operation, the FPD 27 restarts the resetting operation.

The image data transmitted to the image acquisition controller 23 is further transferred to the console 24. In the console 24, the image data is rendered with the offset correction, gain correction and other various processes, and then served for displaying the endoscopic image or stored in an appropriate data storage device.

The switching hub 25 intermediates the signal transmission between the electronic cassette 21 and the image acquisition controller 23. The image acquisition controller 23 sends out a signal along with destination data designating one of the electronic cassettes 21. Then the switching hub 25 sorts the signal from the image acquisition controller 23 and sends it to the designated cassette 21. Likewise, signals from the electronic cassettes 21, including the image data, are transmitted to the image acquisition controller 23 by way of the switching hub 25.

As described so far, the image acquisition controller 23 is provided separately from the power supplies 34 for the three electronic cassettes 21, and the communication cables 29 connected to the cassettes 21 and the communication cable 30 connected to the image acquisition controller 23 are collected together at the switching hub 25 such that the switching hub 25 intermediates the signal transmission between the electronic cassettes 21 and the image acquisition controller 23. Thus, it becomes possible to supervise the operation of the individual electronic cassettes 21 using only one image acquisition controller 23. Consequently, the x-ray radiography system 10 can save the space and cost while managing multiple electronic cassettes.

In the above-described first embodiment, the power cable 35 and the communication cable 29 are separately connected to the electronic cassette 21. However, the need for attaching and detaching the two cables can lower the operability and convenience of the electronic cassette 21. Especially in the case where the electronic cassette 21 should be positioned on a bed on which the test subject H lies, or the electronic cassette 21 should be held by the test subject H during the exposure, the two cables connected to the cassette 21 must be a burden to the radiologist.

Figure 5:
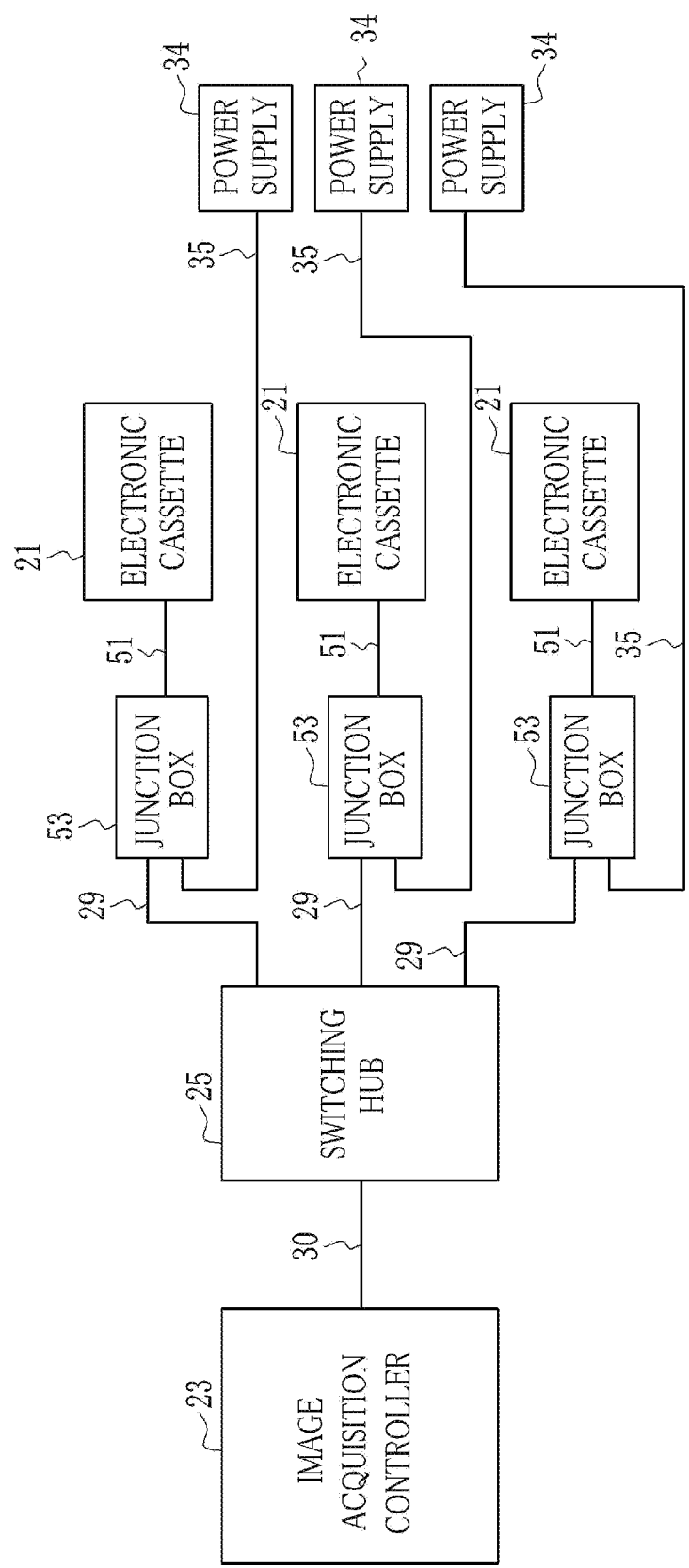
FIG. 5 is a block diagram illustrating a second embodiment of the invention, wherein each electronic cassette is connected to a junction box as an interface to a communication cable and a power cable.
Figure 6:
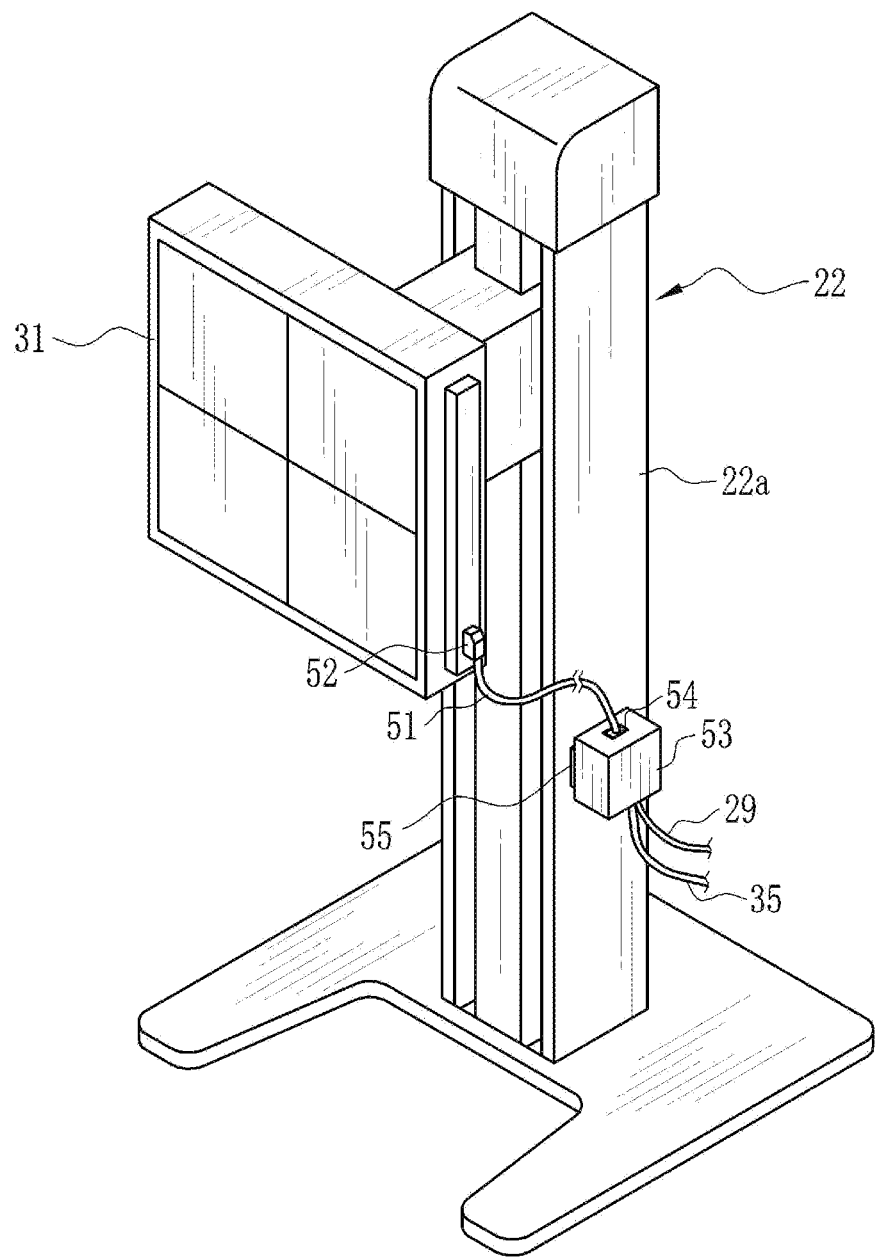
FIG. 6 is a perspective view of a radiographic stand mounted with an electronic cassette and a junction box.

In the second embodiment, as shown in FIGS. 5 and 6, a composite cable 51 bundling the power cable 35 and the communication cable 29 together is connected to the electronic cassette 21 through a connecter 52 that is provided at one end of the composite cable 51. The composite cable 51 is connected to a junction box (first transporter) 53 through another connector 54 provided at the opposite end. The junction box 53 serves as an interface of the electronic cassette 21 to the power supply 34 and the image acquisition controller 23. Inside the junction box 53, the composite cable 51 is branched into the power cable 35 and the communication cable 29.

The junction box 53 may be attached to any appropriate position, e.g. on a side wall of a pillar 22a of the radiographic stand 22, where the junction box 53 will not interfere with the electronic cassette 21 to beheld in the holder 31. The junction box 53 may preferably be detachably attachable using a well-known mounting member 55, such as magnet, suction pad, rubber band, adhesive tape etc. For radiography using a radiographic table, the junction box 53 may be attached to a leg of the radiographic table or on a bottom side or a lateral side of a tray of the radiographic table, the tray holding the electronic cassette 21.

Because the electronic cassette 21 is required to have just one composite cable 51 connected thereto, the second embodiment will improve the operability of the electronic cassette 21 over the first embodiment that requires individual connection of the power cable 35 and the communication cable 29 to the electronic cassette 21. Making the junction box 53 easy to attach to and detach from the radiographic stand 22 enables applying the x-ray radiography system of the present embodiment, which uses the junction box 53 and the switching hub 25, to conventional electronic cassettes that use the composite cable 51.

As the junction box 53 may be attached to the radiographic stand 22, the composite cable 51 has only to extend over a short distance between the electronic cassette 21 and the radiographic stand 22, and the power cable 35 and the communication cable 29 may separately extend from the radiographic stand 22. Therefore, the communication cable 29 may be wired along the shortest and easiest route from the radiographic stand 22 to the switching hub 25. Likewise, the power cable 35 may be wired along the shortest route from the radiographic stand 22 to the power supply 34. Thus, the risk of interference of the cables 29 and 35 with other medical equipment is suppressed to the minimum. The second embodiment permits more flexible arrangement of the system components, including the cables, making it easier to arrange the system components so as not to hinder the operation or movement of the radiologist or the patient or test subject.

Figure 7:
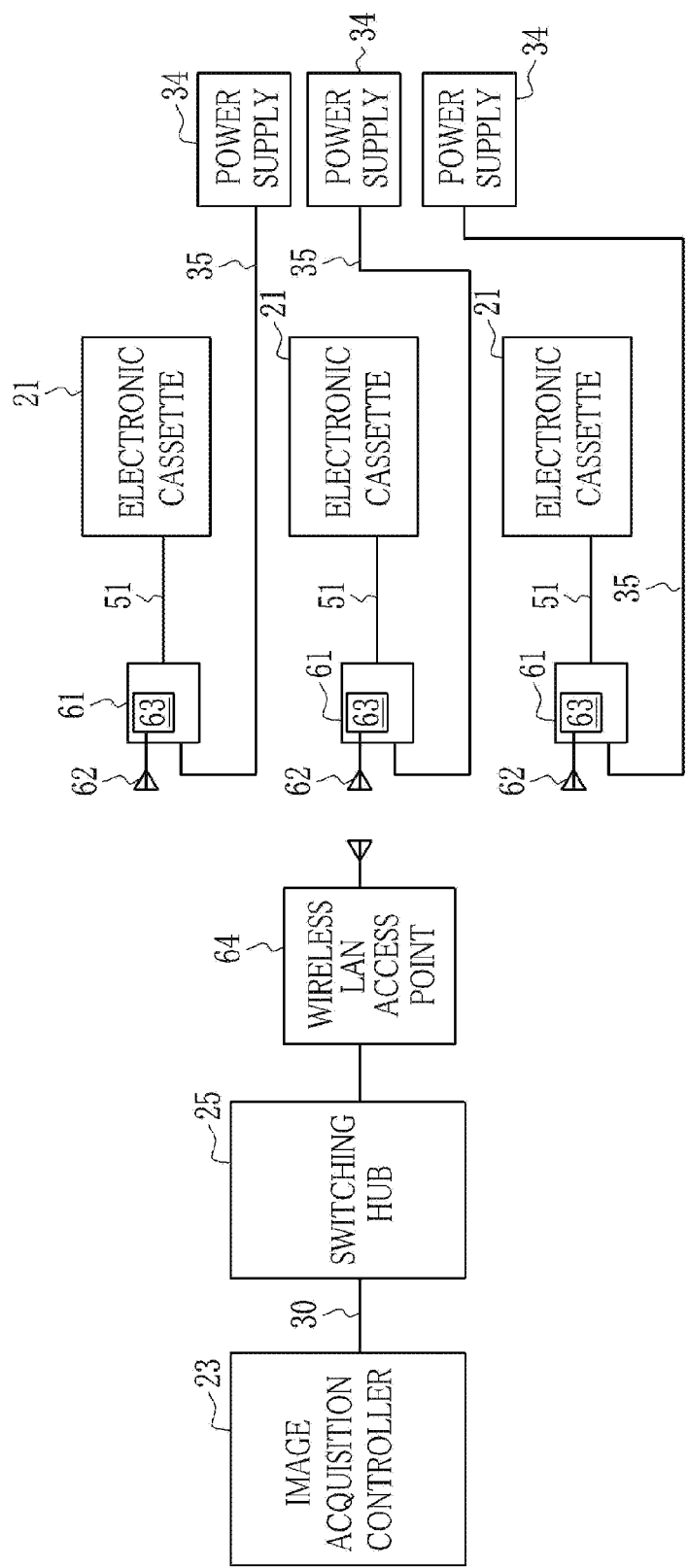
FIG. 7 is a block diagram illustrating another embodiment of the invention, wherein each electronic cassette is connected to a junction box having a wireless communication device.

Alternatively, the composite cable 51 may be connected to a junction box (second transporter) 61 having a wireless communication device, as shown in FIG. 7. For example, the junction box 61 is provided with an antenna 62 and a wireless communicator 63, through which the junction box 61 can wirelessly transmit signal to and from an access point 64 of a wireless LAN that is connected to the switching hub 25. In this embodiment, the wireless communicator 63 is power-supplied from the power supply 34.

The configuration of FIG. 7 enables wireless communication with such electronic cassettes that do not have any wireless communication device. Providing the wireless communication device in the junction box 61 will reduce the distance from the electronic cassette 21 to the wireless LAN access point 64 by the length of the composite cable 51 as compared to the case where the wireless communication device is provided in the electronic cassette 21. The reduced distance to the LAN access point 64 is effective to keep the condition for wireless communication well. Because the junction box 61 can be mounted outside the radiographic stand 22, obstacles against electric waves for the wireless communication will be reduced in comparison with the case where the wireless communication device is provided in the electronic cassette 21. This is also effective to keep the condition for wireless communication well. Moreover, because the wireless communication device in the junction box 61 may be supplied with power from the power supply 34 that is connected to the external commercial power source, there is no need for loading any battery in the electronic cassette 21 in order to enable wireless communication between the cassette 21 and the image acquisition controller 23. That is, there is no need for reloading or recharging the battery.

However, under some circumstances, it can be difficult to connect the electronic cassette 21 to the power supply 34. Therefore, it may be preferable to provide the electronic cassette 21 with a battery for supplying power in case where the connection between the electronic cassette 21 and the power supply 34 is difficult. It is preferable to provide the electronic cassette 21 with a device for detecting whether the electronic cassette 21 is connected to the power supply 34 or not, so that the built-in battery may be automatically used for supplying the electronic cassette 21 when the power supply 34 is not connected to the electronic cassette 21.

In an alternative embodiment, it is possible to provide the two kinds of junction boxes 53 and 61 in the x-ray radiography system, although either the junction boxes 53 or the junction boxes 61 are used in the embodiment illustrated in FIG. 5 or 7.

Figure 8:
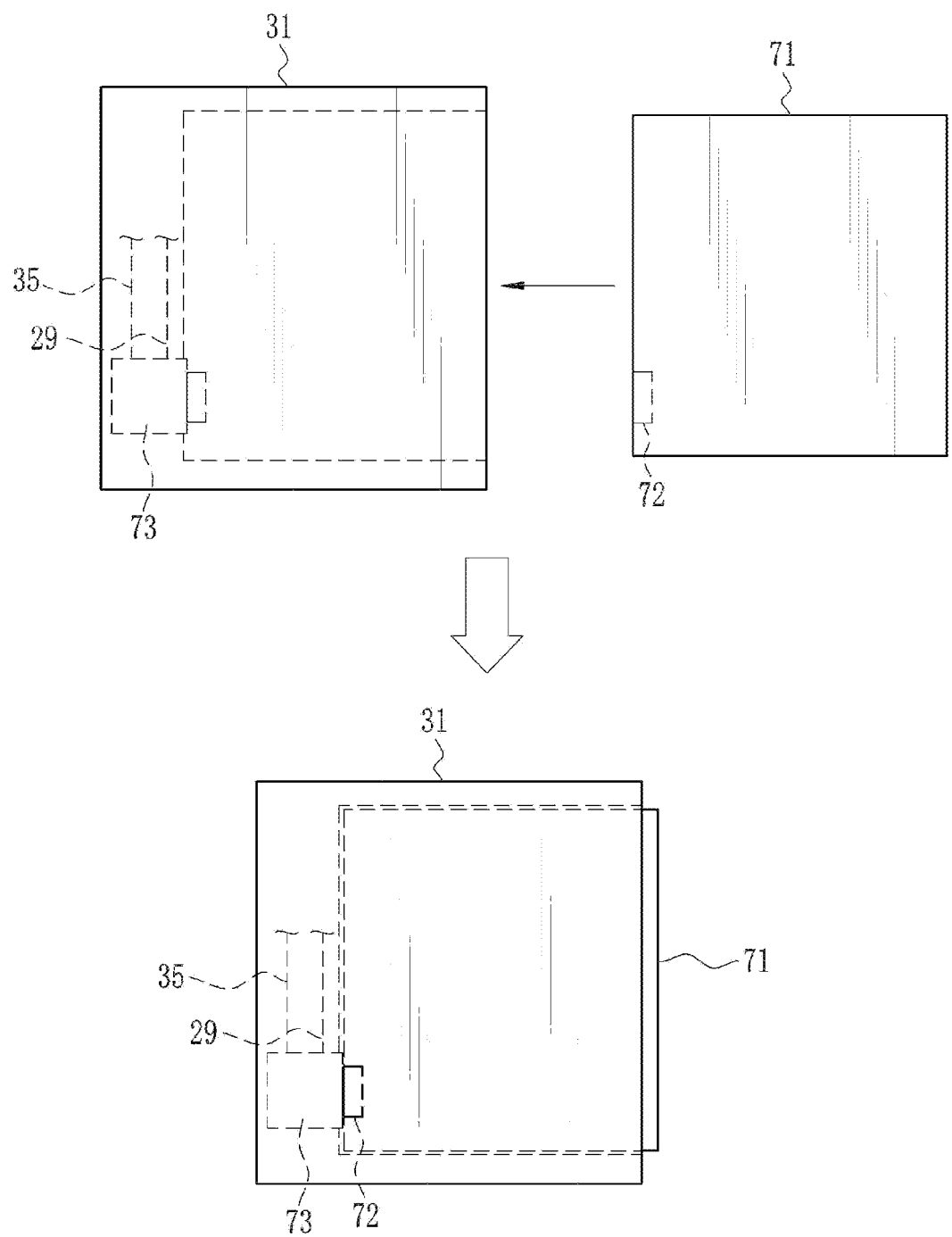
FIG. 8 is an explanatory diagram illustrating an embodiment, wherein a cable connector is provided in a holder of a radiographic stand.

In another embodiment, as shown in FIG. 8, a connector 73 is provided inside a holder 31 of a radiographic stand 22, such that the connector 73 will be plugged in a socket 72 of an electronic radiography cassette 71 as mounted in the holder 31. The socket 72 of the cassette 71 doubles as a connector for power supply and a connector for signal communication, and the connector 73 inside the holder 31 is connecting the electronic cassette 71 to the power cable 35 and the communication cable 29. The power cable 35 and the communication cable 29 extend from the connector 73 through a channel inside the holder 31 and the pillar 22a, and are drawn out for example from a lower outlet of the pillar 22a. In this embodiment, the radiographic stand 22 functions like a junction box, so that it is unnecessary to connect any cable to the electronic cassette 21. Thus, this embodiment further improves the operability and convenience of the electronic cassette 21.

Figure 9:
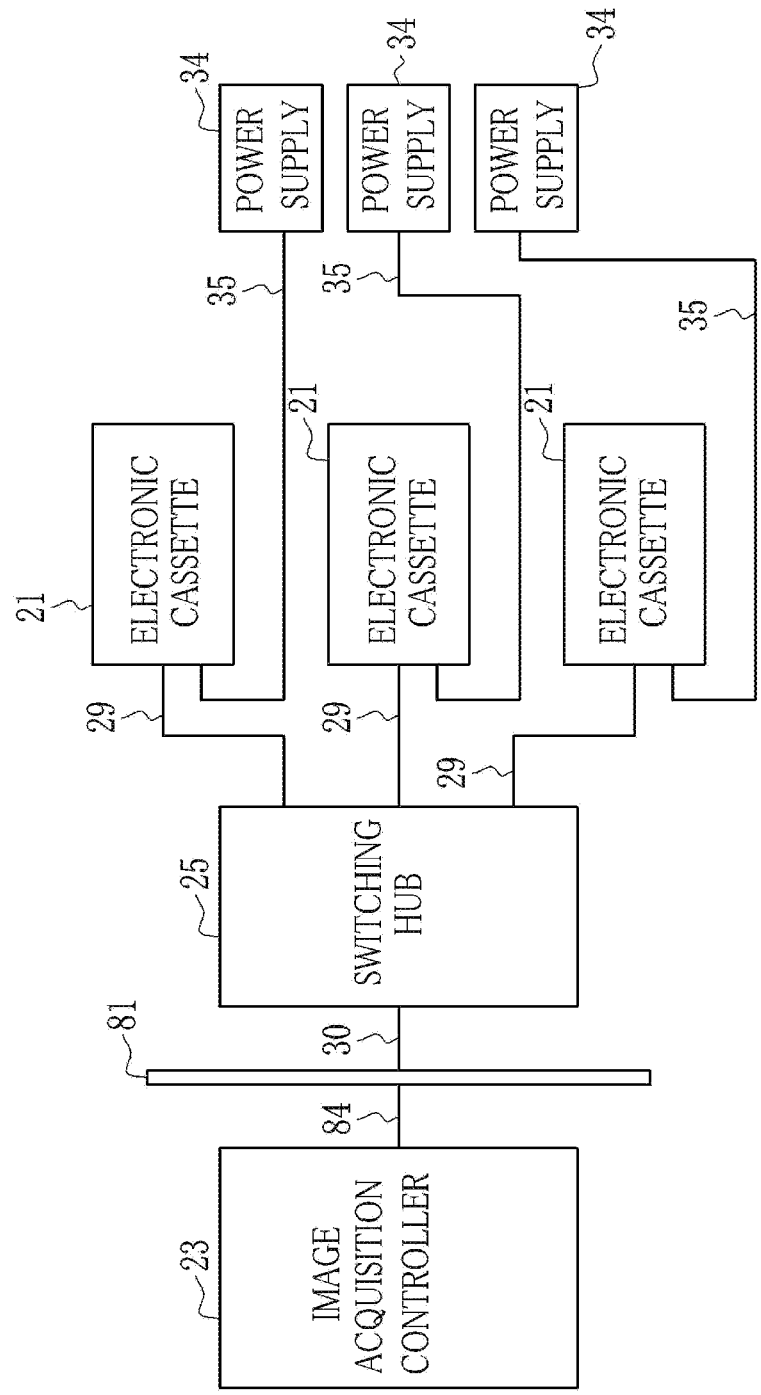
FIG. 9 is a block diagram illustrating a further embodiment of the invention, wherein an image acquisition controller and a switching hub are interconnected through an intra-hospital LAN.
Figure 10:
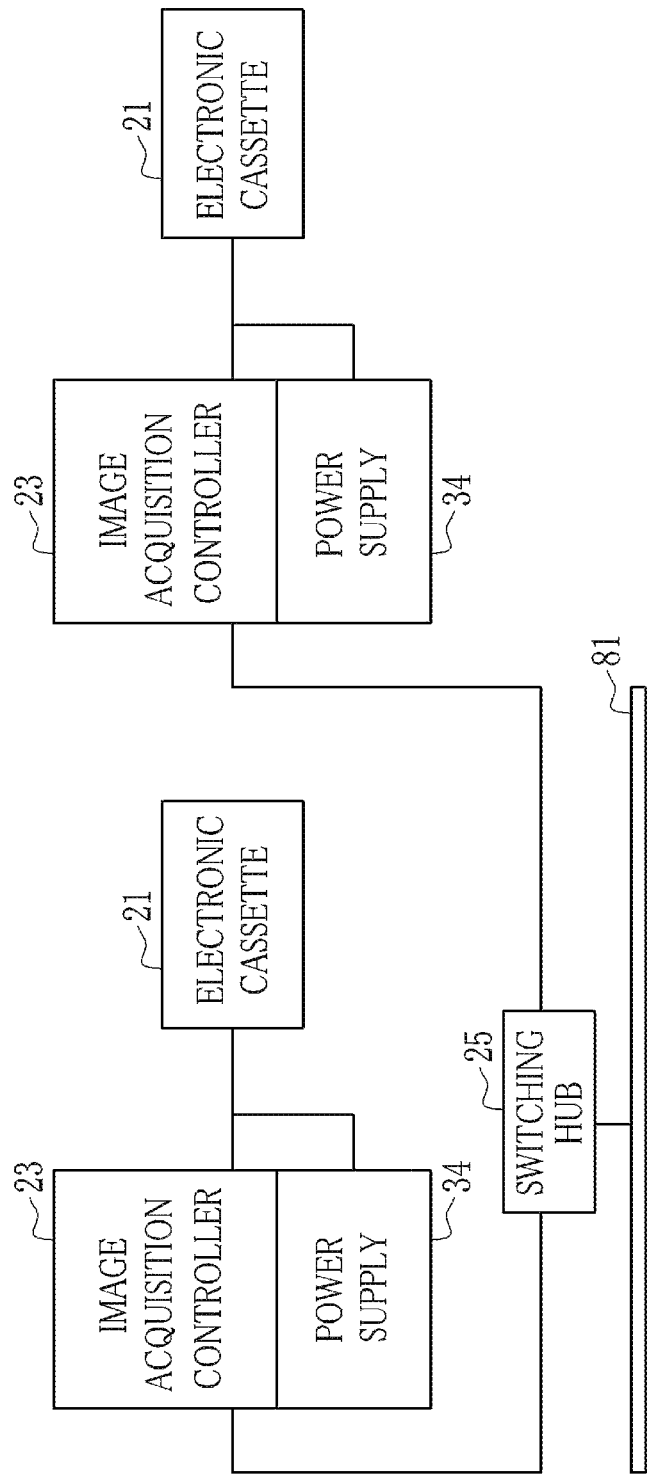
FIG. 10 is a block diagram illustrating the circuitry of a conventional radiographic apparatus as a comparative example to the embodiment of FIG. 9.

As shown in FIG. 9, the image acquisition controller 23 and the switching hub 25 may be interconnected through an intra-hospital LAN 81 developed in a hospital. Then, the image acquisition controller 23 can access a hospital information system (HIS) or a radiological information system (RIS) of the hospital. In a conventional radiographic apparatus, as shown in FIG. 10, there is no switching hub that intermediates the communication between electronic cassettes 210 and image acquisition controllers 230, but a switching hub 250 is connected to an intra-hospital LAN 810, and the image acquisition controller 230 is connected to the electronic cassette 210 and the switching hub 250 through respective connectors.

In contrast to the conventional radiographic apparatus, the radiographic apparatus shown in FIG. 9 just needs to connect the image acquisition controller 23 to the LAN 81 through a cable 84. Therefore, if necessary, the image acquisition controller 23 may be replaced with a new one without any complicated re-wiring or re-arrangement of the radiographic apparatus.

It should be appreciated that the radiographic apparatus of the invention may use more than three electronic cassettes. A repeater hub may be used as a line concentrator in place of the switching hub.

Moreover, the radiographic apparatus of the present invention may not necessarily include the line concentrator. For example, in the first embodiment shown in FIG. 4, the communication cables 29 may also be directly connected to the image acquisition controller 23. In that case, the image acquisition controller 23 should preferably be provided with multiple connectors for connection of these communication cables 29. As for the second embodiment shown in FIG. 5, three communication cables may extend from the image acquisition controller 23 to the respective junction boxes 53. In the embodiment shown in FIG. 8, multiple communication cables may extend from the image acquisition controller 23 to individual radiographic stands 22.

There have been such kinds of x-ray sources that do not need the warm-up operation, such as fixed anode type and cold cathode type. With this kind of x-ray source, the activation switch may merely have a function to output a radiation start signal. Even while the x-ray source needs the warm-up operation, the activation switch may not necessarily output a warm-up start signal but may merely output a radiation start signal to the radiation source controller if the radiation source controller is configured to start the warm-up operation of the x-ray source in response to the radiation start signal and then start x-ray radiation automatically when the warm-up operation is complete.

Although the present invention has been described with reference to those embodiments wherein the electronic cassette and the image acquisition controller are configured as separate components, it is possible to integrate some function of the image acquisition controller into a control circuit that is built in the electronic cassette.

Moreover, the present invention is applicable not only to x-ray radiography systems but also to other radiography systems using other kinds of radioactive rays like gamma-rays.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

What is claimed is:

1. A radiographic apparatus comprising:
    a power cable connectable to an electronic cassette;
    a power supply for supplying power to the electronic cassette, the power supply being connected directly with the power cable;
    a communication cable provided separately from the power cable; and
    an image acquisition controller for controlling operation of the electronic cassette, the image acquisition controller being communicable with the electronic cassette through the communication cable to a plurality of users.

2. The radiographic apparatus of claim 1, wherein the radiographic apparatus includes multiple power supplies, the same number of power cables and the same number of communication cables as the power supplies, and only one image acquisition controller.

3. The radiographic apparatus of claim 2, further comprising a line concentrator for intermediating communication between the image acquisition controller and multiple electronic cassettes through the communication cables.

4. The radiographic apparatus of claim 3, wherein communication cables connectable to the electronic cassettes and a communication cable directly connected with the image acquisition controller are connected to each other at the line concentrator.

5. The radiographic apparatus of claim 3, wherein a composite cable bundling a communication cable and a power cable into a string is connectable to an electronic cassette, and the radiographic apparatus further comprises a first transporter that connects with the composite cable to separate the composite cable into the communication cable and the power cable, wherein the communication cable from the transporter and a communication cable directly connecting with the image acquisition controller are connected to each other at the line concentrator.

6. The radiographic apparatus of claim 5, wherein the first transporter is mounted on or in a radiographic cassette holding device, to which an electronic cassette is detachably attachable.

7. The radiographic apparatus of claim 5, wherein the first transporter is detachably attachable to a radiographic cassette holding device, to which an electronic cassette is detachably attachable.

8. The radiographic apparatus of claim 1, wherein a composite cable bundling a communication cable and a power cable into a string is connectable to an electronic cassette, and the radiographic apparatus further comprises a first transporter that connects with the composite cable to separate the composite cable into the communication cable and the power cable, wherein the communication cable from the transporter is directly connected with the image acquisition controller, and the power cable from the transporter is directly connected with the power supply.

9. The radiographic apparatus of claim 3, wherein a composite cable bundling a communication cable and a power cable into a string is connectable to an electronic cassette, and the radiographic apparatus further comprises a second transporter having a wireless communication device and a wireless LAN for communication with the wireless communication device of the second transporter, wherein an access point of the wireless LAN and a communication cable directly connecting with the image acquisition controller are connected to each other at the line concentrator.

10. The radiographic apparatus of claim 9, wherein the second transporter is mounted on or in a radiographic cassette holding device, to which the electronic cassette is detachably attachable.

11. The radiographic apparatus of claim 9, wherein the second transporter is detachably attachable to a radiographic cassette holding device, to which the electronic cassette is detachably attachable.

12. The radiographic apparatus of claim 3, wherein a radiographic cassette holding device for detachably attaching an electronic cassette is provided with a connector, the connector being connected with a socket of the electronic cassette to connect the electronic cassette to the communication cable and the power cable when the electronic cassette is attached to the radiographic cassette holding device, wherein the communication cable extending from the connector and a communication cable directly connecting with the image acquisition controller are connected to each other at the line concentrator.

13. The radiographic apparatus of claim 1, wherein a radiographic cassette holding device for detachably attaching an electronic cassette is provided with a connector, the connector being connected with a socket of the electronic cassette to connect the electronic cassette to the communication cable and the power cable when the electronic cassette is attached to the radiographic cassette holding device, wherein the communication cable and the power cable extending from the connector are respectively connected directly with the image acquisition controller and the power supply.

14. The radiographic apparatus of claim 3, wherein the image acquisition controller and the line concentrator are connected to each other through a LAN that is developed within a hospital.

* * * * *